(12) United States Patent
Ko et al.

(10) Patent No.: US 7,697,130 B2
(45) Date of Patent: Apr. 13, 2010

(54) APPARATUS AND METHOD FOR INSPECTING A SURFACE OF A WAFER

(75) Inventors: Woo-Seok Ko, Yongin-si (KR); Yu-Sin Yang, Seoul (KR); Young-Jee Yoon, Anyang-si (KR); Chung-Sam Jun, Anyang-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 0 days.

(21) Appl. No.: 12/368,020

(22) Filed: Feb. 9, 2009

(65) Prior Publication Data
US 2009/0219520 A1     Sep. 3, 2009

(30) Foreign Application Priority Data
Feb. 28, 2008    (KR) .................. 10-2008-0018119

(51) Int. Cl.
*G01N 21/88* (2006.01)
*G06F 19/00* (2006.01)

(52) U.S. Cl. ................. 356/237.5; 356/237.4; 356/394; 702/35

(58) Field of Classification Search ... 356/237.1–237.6, 356/394; 250/559.31, 559.41; 702/35
See application file for complete search history.

(56) References Cited
U.S. PATENT DOCUMENTS
5,038,048 A * 8/1991 Maeda et al. .......... 250/559.41

| | | | | |
|---|---|---|---|---|
| 5,355,212 A * | 10/1994 | Wells et al. | ............... | 356/237.4 |
| 6,263,099 B1 * | 7/2001 | Maeda et al. | ............... | 382/149 |
| 6,544,802 B1 * | 4/2003 | Jun et al. | ...................... | 438/14 |
| 6,909,798 B1 * | 6/2005 | Yukawa et al. | ............. | 382/141 |
| 7,170,593 B2 * | 1/2007 | Honda et al. | ............. | 356/237.1 |
| 7,330,248 B2 * | 2/2008 | Sakai et al. | ............. | 356/237.4 |
| 7,433,032 B2 * | 10/2008 | Kim et al. | ................ | 356/237.2 |
| 2007/0188832 A1 | 8/2007 | Hayakawa et al. | | |

FOREIGN PATENT DOCUMENTS

| JP | 2003-270172 | 9/2003 |
|---|---|---|
| KR | 2000-0014554 | 3/2000 |

\* cited by examiner

*Primary Examiner*—Sang Nguyen
(74) *Attorney, Agent, or Firm*—F.Chau & Associates, LLC

(57) ABSTRACT

A surface inspection apparatus and method increase wafer productivity, wherein to increase an efficiency of the surface inspection apparatus to detect defects during a scanning of the wafer surface, a scanning speed for a subsequent defect detection is varied according to an increase/decrease of defect density represented on a plurality of images acquired successively. When the density of defects is reduced, the scanning speed increases and a level of a skip rule increases, and when the density of defects increases, the scanning speed decreases and a level of the skip rule decreases to precisely detect defects, thereby increasing reliability, throughput, and productivity.

17 Claims, 4 Drawing Sheets

APPARATUS AND METHOD FOR INSPECTING A SURFACE OF A WAFER

CROSS-REFERENCE TO RELATED APPLICATION

This application claims priority under 35 U.S.C. §110 of Korean Patent Application No. 10-2008-0018119, filed on Feb. 28, 2008, the entire contents of which are hereby incorporated by reference.

BACKGROUND

The recent integration increase of semiconductor devices causes an operation defect of semiconductor devices due to a minute defect that was not such a serious problem in the past, but has a very bad influence upon reliability of the semiconductor devices with a high degree of integration. Defects generated in semiconductor device manufacturing processes may be, for example, foreign particles, a void, dislocation, a stacking fault, an interface fault and the like.

Generally, a surface fault is inspected and measured before or after unit processes of a semiconductor device are performed. A research and development for surface inspection apparatuses to rapidly and precisely detect defects has been actively progressing. It can be understood that the reliability of semiconductor devices depends upon the accurate performance of such surface inspection apparatuses.

Most surface inspection apparatuses employ a bright field optical system for acquiring an image from light reflected from the wafer surface by directing light of a high illumination onto the wafer surface. The bright field optical system uses the reflected light to reproduce an image of the surface. Meanwhile, when employing a dark field optical system using light scattered from defects it is difficult to reproduce an actual image of the wafer surface. Thus, the bright field optical system may be the best way to detect defects on the wafer surface on which various kinds of patterns are formed.

The surface inspection apparatus employing the bright field optical system performs a line scan for a wafer surface by using an image acquisition system, such as a CCD (Charge-coupled device) or TDI (Time Delay Inspection) sensor, so as to detect defects present on an entire face of the wafer. A wafer surface defect detection using such surface inspection apparatus is performed by selecting and sampling a selected area, except for a given portion according to a given skip rule. This is why a defect detection time is long when performing a precise defect inspection for an entire face of a wafer using the image acquisition system of high sensitivity. Thus, a testing throughput decreases.

For example, the TDI sensor uses a swath sampling with a constant scan line interval. A swath sampling of about 25% for the entire face of a wafer is performed according to a skip rule, thereby shortening the defection detection time and thereby increasing a testing throughput.

In the surface inspection apparatus and method described above, however, a throughput can be just enhanced by reducing a scan measurement area when applying a given skip rule, such as swath sampling, but a large amount of defects cannot be detected by an increased skip rule and, thus, a reliability of the defect detection decreases.

Furthermore, when a large amount of defects concentrated mainly on a partial surface, such as an edge portion of a wafer cannot be completely detected, errors in semiconductor manufacturing processes occur and, thus, a production yield decreases.

SUMMARY OF THE INVENTION

The present disclosure relates to surface inspection apparatuses and, more particularly, to a surface inspection apparatus and method involving varying a scanning speed according to a defect density present on a wafer surface.

Exemplary embodiments of the present invention provide a surface inspection apparatus and a surface inspection method thereof capable of increasing reliability in detecting a large amount of impurities and, thus, increasing productivity. In addition, a large amount of impurities concentrated on a partial surface of a wafer can be detected, thereby preventing errors in a semiconductor manufacturing process.

According to an exemplary embodiment of the present invention, a surface inspection apparatus comprises a stage for supporting and horizontally moving a wafer; an optical system for enlarging and projecting the surface of the wafer supported on the stage; an image acquisition system for acquiring image data of the wafer surface projected from the optical system; an image processing unit for processing an image corresponding to the wafer surface by using the image data acquired in the image acquisition system; a defect-detecting unit for detecting defects of the wafer surface generated on the image processed in the image processing unit; a defect density-counting unit for computing a density of defects detected by the defect-detecting unit; a density comparison unit for comparing a corresponding defect density of the image calculated in the defect density-counting unit with a previous defect density acquired in a preceding defect measurement; and a scanning speed decision unit for varying a horizontal moving speed of the stage according to a difference between the corresponding defect density and the previous defect density compared in the density comparison unit and thereby deciding a scanning speed of the image acquisition system.

The surface inspection apparatus may further comprise a database for storing the previous defection density for comparison with the corresponding defection density in the density comparison unit.

According to an exemplary embodiment of the present invention, a surface inspection method comprises enlarging and projecting a given position of a wafer supported on a stage, and acquiring image data corresponding to the given position of the wafer by an image acquisition system; processing a corresponding image in an image processing unit by using the image data; detecting defects of the wafer surface generated on the corresponding image in a defect-detecting unit; computing a density of defects detected from the corresponding image in a defect density-counting unit; comparing a defect density of a previous image acquired in a defect detection performed before acquiring the corresponding image with a defect density of the corresponding image in a density comparison unit; and varying a horizontal moving speed of the stage according to a difference of defect densities in a defect detection performed by using a subsequently acquired image and thereby controlling a scanning speed.

When the defect density of the corresponding image is reduced as compared with the defect density of the previous image, a scanning speed of the image acquisition system increases, and when the defect density of the corresponding image increases as compared with the defect density of the previous image, a scanning speed of the image acquisition system is reduced. Additionally, when the defect density of the corresponding image is the same as, or similar to, the defect density of the previous image, a horizontal movement of the stage of the image acquisition system may be maintained at the same speed.

According to an exemplary embodiment of the present invention, a surface inspection method comprises loading a wafer on a predetermined position of a stage; determining a scanning section for an inspection area corresponding to a patterning area of the wafer; enlarging and projecting a surface of the wafer within the scanning section, and acquiring an image corresponding to a surface of the wafer and then starting a scan by an image acquisition system; detecting a defect of the image in a defect-detecting unit; computing a density of defects in a defect density-counting unit; comparing an increase/decrease of the defect density in a density comparison unit; and varying a scanning speed according to an increase/decrease result of the defect density.

As described above, according to exemplary embodiments of the present invention, a moving speed of the stage is varied as a density of defects generated on a wafer surface is changed, and a scanning speed of the image acquisition system is varied, thereby increasing reliability in performing defect detection and increasing throughput and productivity.

In addition, a large amount of impurities concentrated on a partial surface of the wafer can be detected, thereby preventing errors in a semiconductor manufacturing process.

BRIEF DESCRIPTION OF THE DRAWINGS

Exemplary embodiments of the present invention will become more fully understood from the following descriptions taken in conjunction with the accompanying drawings which are given by way of illustration only, and thus are not limitative of the present invention, and wherein.

DETAILED DESCRIPTION OF EXEMPLARY EMBODIMENTS

This application claims priority under 35 U.S.C. §119 from Korean Patent Application 10-2008-0018119, filed on Feb. 28, 2008, the contents of which are hereby incorporated by reference in their entirety as if fully set forth herein.

Exemplary embodiments of the present invention now will be described more filly hereinafter with reference to the accompanying drawings, in which exemplary embodiments of the present invention are shown and like components having like functions have been provided with like reference symbols and numerals. This invention may, however, be embodied in many different forms and should not be construed as limited to the exemplary embodiments set forth herein. Rather these exemplary embodiments are provided so that this disclosure will be thorough and complete, and will fully convey the inventive scope to those of ordinary skill in the art.

Figure 1:
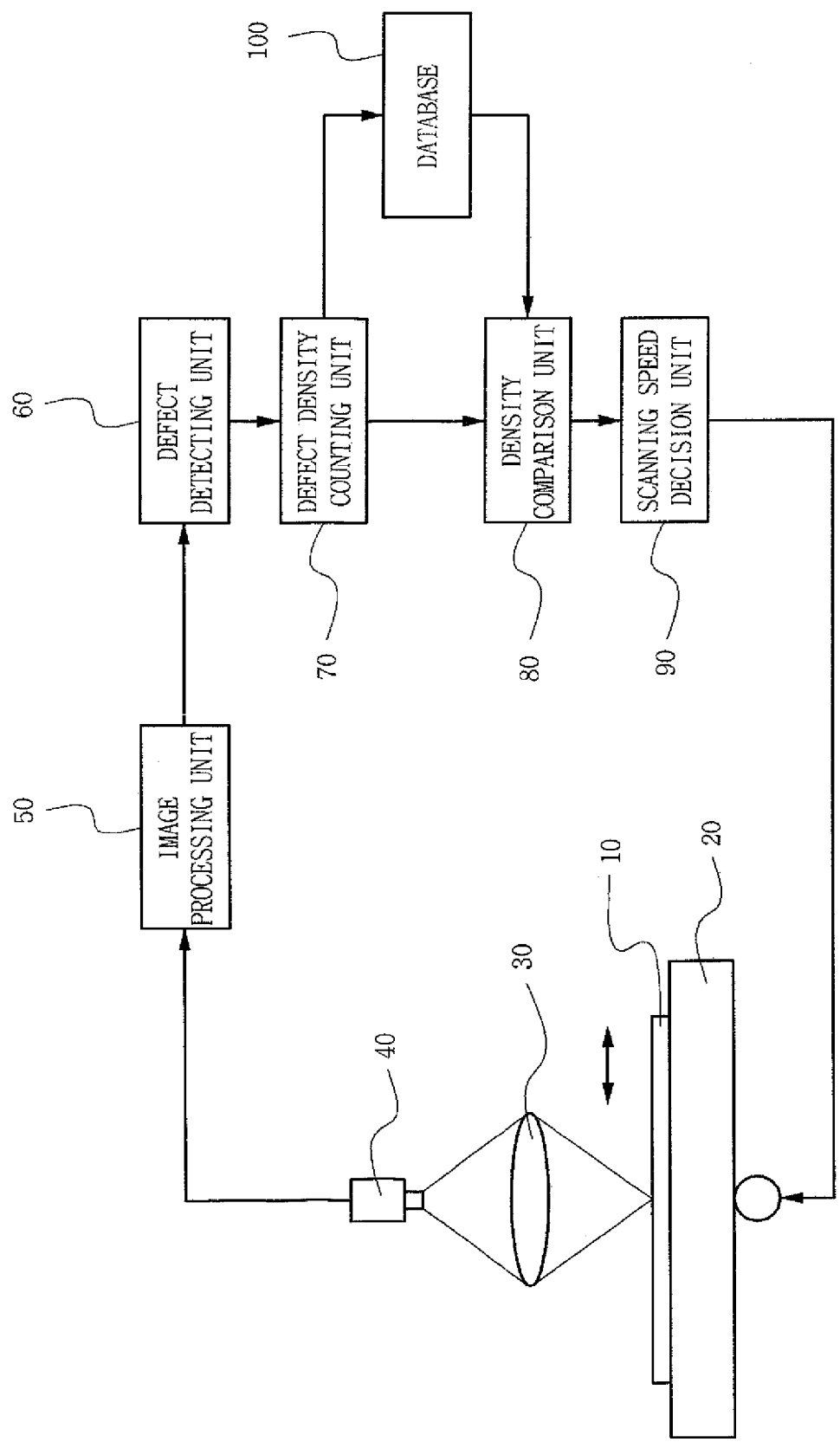
FIG. 1 schematically illustrates a surface inspection apparatus according to an exemplary embodiment of the present invention.

FIG. 1 schematically illustrates a surface inspection apparatus according to an exemplary embodiment of the present invention.

As shown in FIG. 1, a surface inspection apparatus is configured in a way that a horizontal moving speed of a stage 20 supporting a wafer 10 is varied according to a density of defects (110 of FIG. 3) present on the surface of the wafer 10. The surface of the wafer 10 supported on the stage 20 is scanned by an image acquisition system 40 during movement thereof. A scanning speed of the wafer surface may be decided based on the density of defects 110 detected from image data acquired through the image acquisition system 40. At this time, the density of defects 110 is in inverse proportion to a scanning speed. When the defect density is reduced, the scanning speed increases, and when the defect density increases, the scanning speed is reduced.

In a surface inspection apparatus according to an exemplary embodiment of the present invention, a scanning speed can be varied according to a density of defects 110 present on a surface of the wafer 10, thereby simultaneously increasing a detection reliability of defects 110 present on an entire face of the wafer 10 and increasing a testing throughput.

The surface of the wafer 10 supported on the stage 20 is enlarged and projected by an optical system 30. The optical system 30 is formed including a convex lens to enlarge an image of a target by refracting a reflected-light reflected from the surface of the wafer 10. Though not shown in the drawing, an illumination device may be further adapted to illuminate incidence light to an upper part of the stage 20 in the neighborhood of the wafer 10 to produce a reflected light.

The image acquisition system 40 can obtain image data of the wafer surface that is enlarged and projected by the optical system 30. The image acquisition system 40 is a charge-coupled device, typically called an image sensor. For example, the charge-coupled device is provided including a complementary metal oxide semiconductor (CMOS) type image sensor and a charge-coupled device (CCD) type image sensor and the like. The charge-coupled device has a photoelectric conversion function and a scanning function of reading out charge images stored in the pixel groups in which pixels have a charge storing function and are arranged linearly and two-dimensionally. The CMOS image sensor employs an amplifier (not shown), such as a metal oxide semiconductor transistor, in a signal transmission of a light receiving part receiving the reflected light. The CCD image sensor employs a charge-coupled device, such as a diode (not shown). Additionally, the semiconductor device is essentially formed of a single crystal silicon substrate (not shown), and the pixels are formed so as to become a matrix array on the semiconductor substrate. The charge-coupled device generates an output signal current through a sequential read operation based on a scanning method for a charge amount of a pixel as a minimum unit of charge for an image. The charge-coupled device has a function of photoelectric conversion-storage-scan (read). Such method is based on a charge transmission of sequentially transmitting and reading out pixels that are structurally separated/independent one-by-one through a scan signal generator (not shown).

The stage 20 cannot perform a continuous horizontal movement of wafer 10 before one frame is acquired using the charge-coupled device. As the stage 20 horizontally transfers the wafer 10, a portion captured by the charge-coupled device is decided as a section provided by substantially reducing a repeated portion. An operation skipping a given portion is performed to increase a throughput, which is called a skip rule. The amount the skip rule is varied indicates a variation of scanning speed.

On the other hand, image data acquired by the image acquisition system 40 is input to an image processing unit 50 and can be visualized as an image corresponding to a wafer surface at a corresponding position. The visualized image refers to an image acquired within a field of view (FOV) of the image acquisition system 40. A defect-detecting unit 60 detects defects 110 from the image processed in the image processing unit 50. The defect 110 detected in the defect-detecting unit 60 may provide a standard to decide whether or not an operation of semiconductor manufacturing apparatus performing a previous semiconductor manufacturing process is normal. The defect 110 includes particles or voids. The particles are defects, such as various kinds of minute dust particles on the wafer (10) surface generated in the semiconductor manufacturing processes, such as in an etching or deposition process. The defects 110, such as particles or voids are formed protruded or recessed in some level from a flat face of the wafer surface, and thus are represented as excessively dark or light as compared with a periphery area within an image.

Thus the defect-detecting unit 60 can detect defects 110 irregularly located on an image corresponding to the wafer 10 surface. The defect-detecting unit 60 decides as the defect 110, particles or voids of a constant or irregular size generated within an image, and counts the number of the defects 110 or an area of the defects 110. Additionally, when the size of a corresponding defect 110 is excessively large, the defect 110 may be divided into several defects 110. Moreover, the defect-detecting unit 60 can divide one image corresponding to one visual range into a plurality of segments and counts the number of defects existing in the respective segments or an area thereof.

A defect density-counting unit 70 computes the number or area of defects 110 per unit area, and detects the density of the defects 110. In this exemplary embodiment, the density of defects can be acquired by counting the number of defects generated in a corresponding image or computing a defect area rate of the corresponding image. Similarly, the defect density-counting unit 70 can count the density of defects existing in a plurality of respective segments obtained by dividing a corresponding image. The defect density-counting unit 70 outputs information corresponding to the density of the defects 110 detected from the corresponding image to a density comparison unit 80 and to a database 100. The database 100 temporarily stores therein information corresponding to the density of the defects 110 detected from the corresponding image, and when subsequent information corresponding to the density of the defects 110 detected from a subsequent image is input, the database 100 outputs the corresponding information to the density comparison unit 80.

The density comparison unit 80 compares information corresponding to a density of the defects 110 detected in a corresponding image input from the defect density-counting unit 70, with previous information corresponding to a density of the defects 110 detected in a previous image input from the database 100. According to a comparison result of the previous information and the corresponding information, a subsequent scanning speed decision unit 90 can decide a moving speed of the stage 20. Additionally, the scanning speed decision unit 90 can decide a moving speed of the stage 20 according to a comparison result of defect density differences in a plurality of segments of the corresponding image. This is the same as deciding a moving speed of the stage 20 by using a defect density difference of respective segments of the corresponding image and a previous image.

The scanning speed decision unit 90 may reduce a moving speed of the stage 20 when the density of the defects 110 increases based on the comparison result of the previous information and the corresponding information, and may increase a moving speed of the stage 20 when the density of the defects 110 is reduced. When there is no change in the density of the defects 110, there is no need to vary the moving speed of the stage 20. The scanning speed decision unit 90 is adapted to decide a positional movement of the stage 20 according to density differences compared in the density comparison unit 80. For example, the scanning speed decision unit 90 can vary a scanning speed of the image acquisition system 40 by accelerating or reducing a horizontal moving speed of the stage 20.

Accordingly, the surface inspection apparatus according to exemplary embodiments of the present invention varies a moving speed of the stage 20 according to a change in the density of the defects 110 present on the surface of the wafer 10 and also varies a scanning speed of the image acquisition system 40, thereby increasing the reliability of defect detection and improving throughput, thus increasing productivity.

Additionally, a large amount of impurities that are concentrated in a partial portion can be detected, thereby preventing errors in a semiconductor manufacturing process.

A surface inspection method using the surface inspection apparatus is described as follows, according to an exemplary embodiment of the present invention.

Figure 2:
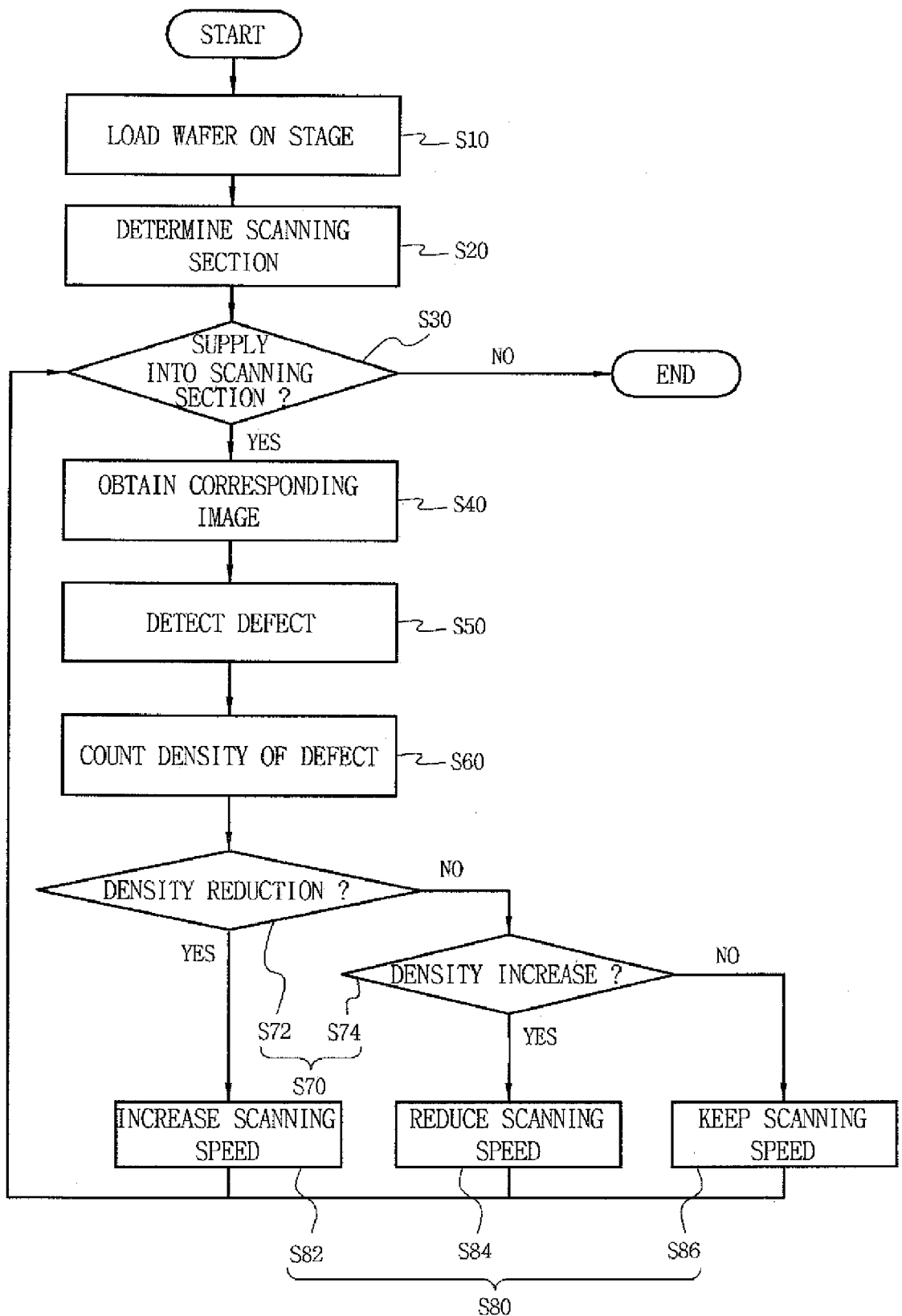
FIG. 2 is a flowchart providing a surface inspection method according to an exemplary embodiment of the present invention.

FIG. 2 is a flowchart providing a surface inspection method according to an exemplary embodiment of the present invention.

As represented in FIG. 2, in the surface inspection method according to an exemplary embodiment of the present invention using the apparatus shown in FIG. 1, the wafer 10 is loaded on a predetermined position of the stage 20 in a step S10. The wafer 10 is loaded on the stage 20 so that a flat zone or notch formed at an edge portion of the wafer is directed in a predetermined direction.

Then, a scanning section for an inspection area corresponding to a patterning area of an entire face of the wafer 10 is determined in a step S20. The patterning area is an area in which the semiconductor device is formed and is defined radially from a center of the wafer 10 to given distance, and is constructed of a plurality of dies (130 of FIG. 4) having a repetitive form. For example, the scanning section may be determined from a center of the wafer 10 to a given distance through Cartesian coordinates formed of an X axis and a Y axis.

Then, the optical system 30 and the image acquisition system 40 are positioned at a corresponding position above the wafer 10 and perform a scanning within the scanning section in a step S30. The optical system 30 enlarges and projects an edge surface of the wafer 10 within the scanning section so that an image corresponding to the surface of the wafer 10 is formed in the image acquisition system 40. Thus, the optical system 30 and the image acquisition system 40 are coupled to each other with a given distance.

The image acquisition system 40 obtains image data corresponding to a surface of the wafer 10 of a corresponding position, and the image processing unit 50 processes image data and obtains a corresponding image corresponding to the wafer surface in a step S40. In this exemplary embodiment the image acquisition system 40 can obtain image data of the wafer surface of the horizontally moving stage 20 within a given time interval. This means that a scanning speed of the image acquisition system 40 is changed as the moving speed of the stage 20 is varied. Additionally, a light and darkness of the corresponding image processed in the image processing unit 50 may be represented differently according to an illumination and intensity of a reflected light obtained from an incident light entered from the periphery that is reflected from the surface of the wafer 10.

Then, the defect-detecting unit 60 detects the defects 110 of an image in a step S50. As described above, the defect-detecting unit 60 decides as a defect 110, a portion on which a light and darkness rate is excessively changed as compared with the periphery within a corresponding image that corresponds to a surface of the wafer 10. At this time, an excessively bright or dark portion may be decided as the defect 110. Furthermore, the defect-detecting unit 60 may decide by dividing defects of a constant size or larger size into several defects 110. This is why most defects 110 generated by minute dust, such as particles, are generated with some random size on an entire face of the wafer 10. Additionally, the defect-detecting unit 60 may divide a corresponding image into a plurality of segments and, thus, count the number or area of defects existing in respective segments.

Then, defect density-counting unit 70 counts a density of the defects 110 in a step S60. The defect density-counting unit 70 computes an area or the number of the defects 110 per unit area in a corresponding image and, thus, can obtain a density of the defects 110. In addition, a density of the defects generated in respective pluralities of segments divided from a corresponding image may be counted. For example, when the number of defects 110 is computed and recognized as the density corresponding to the defects 110, a density-counting step may be omitted. When the density of the defects 110 is counted in the defect density-counting unit 70, information corresponding to the density of the defects 110 of the corresponding image is stored in database 100.

Then, the density comparison unit 80 compares an increase/decrease of defect density of a corresponding image in steps S70. The density comparison unit 80 compares information for the defect density of a corresponding image with previous information for a defect density of a previous image input from the database 100. Though not shown in the drawing, when corresponding information initially input to the density comparison unit 80 has no comparison target, the density comparison unit 80 may receive optional previous information from the database 100. There are several methods of comparing the change of defect densities by using corresponding information and previous information. For example, it may be determined in a step S72 whether the density of the defects 110 is reduced, and subsequently it may be determined in a step S74 whether a density of the defects 110 increases. Furthermore, the density comparison unit 80 can compare density differences of defects within the plurality of segments of a corresponding image, or compare density differences of defects within successive segments of the respective corresponding image and the previous image.

Finally, a scanning speed of the scanning speed decision unit 90 is decided by a density comparison result of the density comparison unit 80 in steps S80. That is, when the density is reduced in the comparison result between the corresponding information and the previous information, the scanning speed decision unit 90 increases a moving speed of the stage 20 and so increases a scanning speed in a step S82. When the density increases, a moving speed of the stage 20 is reduced to lessen a scanning speed in a step S84. And, when there is no change in the density, the moving speed of stage 20 is maintained as it is in a step S86. Thereafter, all images corresponding to a patterning area of the entire face of wafer 10 can be acquired by varying the scanning speed according to a density of the defects 110 within the scanning section.

Consequently, the surface inspection method according to an exemplary embodiment of the present invention can increase throughput and productivity by varying a scanning speed according to a detected defect density.

Figure 3:
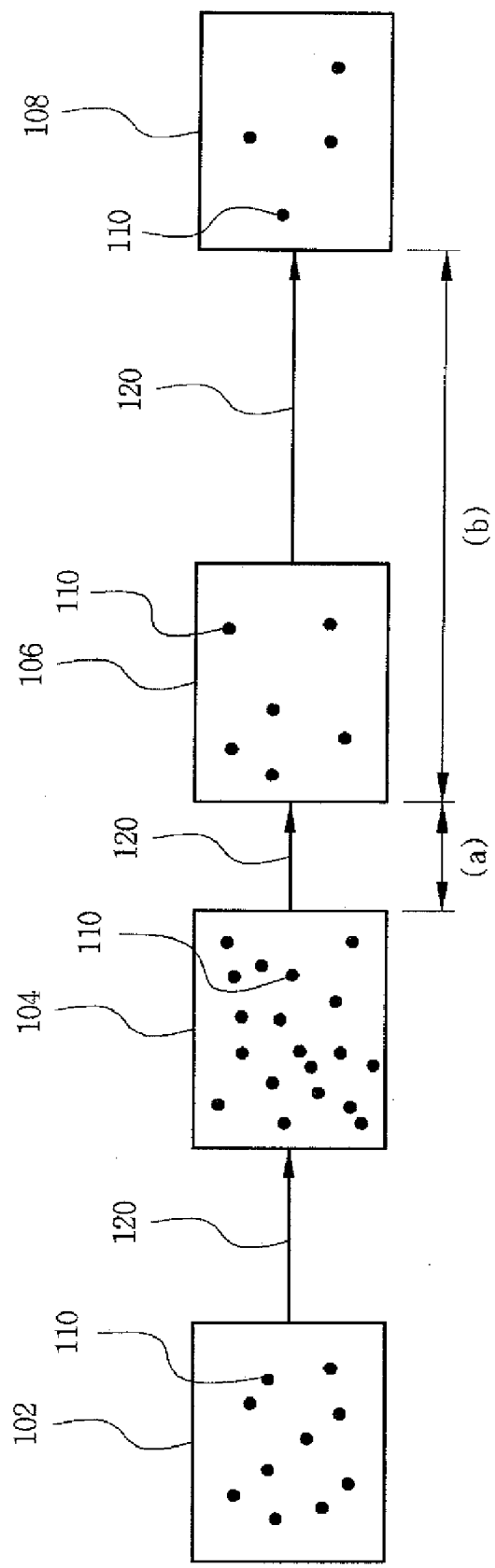
FIG. 3 illustrates a change of scanning speed based on a change of defect density.

FIG. 3 illustrates a change of scanning speed based on a change of defect density. When a density of the defects 110 increases, the scanning speed is reduced to lessen a first sampling distance (a), meanwhile, when the density of the defects 110 is reduced, the scanning speed increases to lengthen a second sampling distance (b). In this exemplary embodiment, the density of the defects 110 is predetermined by a standard for the number of defects 110 having a similar size within one visual range. Furthermore, the defect 110 corresponds to particles present on a specific portion of the entire face of the wafer 10 in a plurality of successive images as shown in FIG. 3. A length of an arrow 120 shown between the successive images may correspond to a scanning speed. For example, the defects 110 shown in a second visual range 104 increase as compared with the defects 110 shown in a first visual range 102, thus, a distance between the second visual range 104 and a subsequent third visual range 106 is reduced as compared with a distance between the first and second visual ranges 102 and 104. The defects 110 represented in the third visual range 106 are reduced as compared with the defects 110 generated in the second visual range 104, thus a distance between the third visual range 106 and a subsequent fourth visual range 108 increases as compared with a distance between the second and third visual ranges 104 and 106.

Accordingly, in a surface inspection method according to an exemplary embodiment of the present invention, when the defect density increases, the scanning speed is reduced and a distance interval for sampling is reduced, thereby precisely detecting a minute defect 110 on a relatively small area. In addition, when the defect density is reduced, the scanning speed increases and the sampling distance is lengthened, thereby performing a relatively slow defect detection on a relatively wide area. When there are almost no defects, as long as the reliability of semiconductor memory device is ensured, a scanning speed is maintained at the maximum speed. In other words, the distance interval for sampling is maximized.

Figure 4:
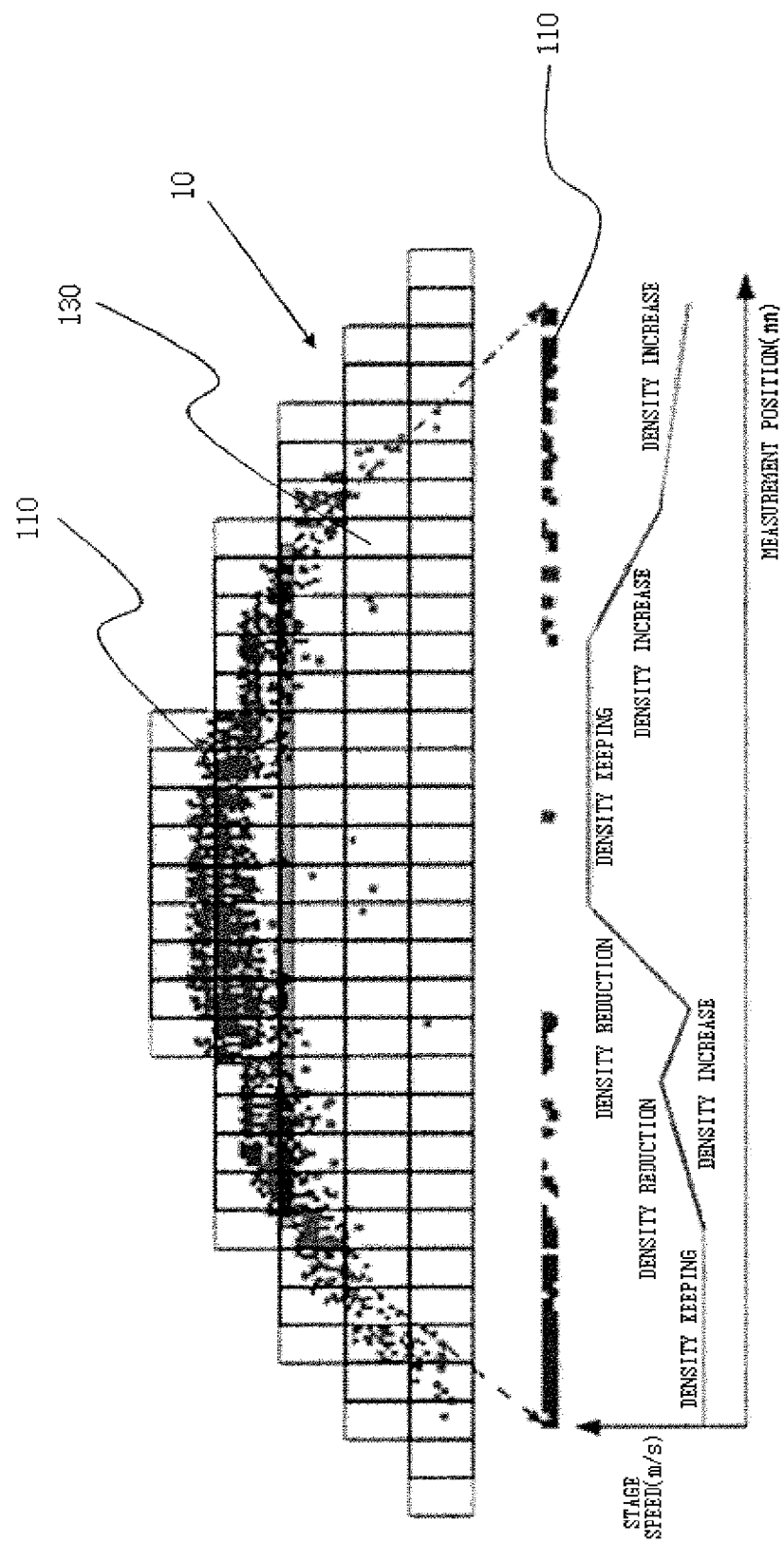
FIG. 4 illustrates a correlation between a density of defects generated at a one-dimensional position of a wafer and a speed of a wafer stage.

FIG. 4 illustrates a correlation between a density of the defects 110 present on one-direction position and a moving speed of the stage 20.

As shown in FIG. 4, a moving speed of the stage 20 is reduced to a relatively lowest level on an edge of the wafer 10 having a high defect density and so the scanning speed is slow, and a moving speed of the stage 20 is increased to a relatively highest level on a center of the wafer 10 having a relatively low defect density and, thus, the scanning speed becomes faster. In FIG. 4 a transverse axis of the graph indicates an X-axis coordinate of the wafer 10, and a longitudinal axis indicates a moving speed of the stage 20. Additionally, a dark portion, such as dots on the wafer 10, indicates a defect 110. It can be noted from FIG. 4 that the moving speed of the stage 20 is varied according to an increase/decrease of the defect density, as shown by the line of defects 110 directly above the speed graph. For example, when the defect density is reduced, a moving speed of the stage 20 is accelerated, and when the defect density increases, such as at the ends of the line of defects 110, the moving speed of the stage 20 is reduced. Further, when the defect density is uniform, the stage 20 moves at a constant speed. That is, the slope of the graph denotes an increased/decreased speed of the stage 20.

Accordingly, in a surface inspection method according to an exemplary embodiment of the present invention and in detecting defects 110 present in large amounts or in small amounts on an edge of a wafer 10, the defects 110 can be precisely detected by reducing the scanning speed at a position corresponding to the edge of wafer 10. In addition, the time taken in the surface inspection can be saved by increasing the scanning speed at a position corresponding to a center of the wafer 10, thereby increasing productivity.

It will be apparent to those of ordinary skill in the art that modifications and variations can be made in the present invention without deviating from the inventive spirit or scope. Thus, it is intended that the present invention cover any such modifications and variations of this invention provided they come within the scope of the appended claims and their equivalents. Accordingly, these and other changes and modifications are seen to be within the inventive true spirit and scope as defined by the appended claims.

In the drawings and specification, there have been disclosed exemplary embodiments of the invention and, although specific terms are employed, they are used in a generic and descriptive sense only and not for limitation, the inventive scope being set forth in the following claims.

What is claimed is:

1. A surface inspection apparatus, comprising:
   a stage for supporting and horizontally moving a wafer;
   an optical system for projecting and enlarging light reflected from a surface of the wafer supported on the stage;
   an image acquisition system for acquiring image data of the wafer surface from the light obtained by the optical system;
   an image processing unit for processing an image corresponding to the wafer surface by using the image data acquired in the image acquisition system;
   a defect-detecting unit for detecting defects of the wafer surface present in the image processed in the image processing unit;
   a defect density-counting unit for computing a density of the defects detected by the defect-detecting unit;
   a density comparison unit for comparing a corresponding defect density of the image computed in the defect density-counting unit with a previous defect density acquired in a preceding defect measurement; and
   a scanning speed decision unit for varying a horizontal moving speed of the stage for a subsequent defect measurement on the basis of a difference between the corresponding defect density and the previous defect density, so as to control a wafer scanning speed, wherein when the corresponding defect density is higher than the previous defect density, the scanning speed decision unit reduces a horizontal moving speed of the stage, and when the corresponding defect density is lower than the previous defect density, the scanning speed decision unit increases a horizontal moving speed of the stage.

2. The apparatus of claim 1, further comprising a database for storing the previous defect density compared with the corresponding defect density in the density comparison unit.

3. A surface inspection method comprising:
   projecting and enlarging light reflected from a given position of wafer supported on a horizontally movable stage, and acquiring image data corresponding to the given position of the wafer by an image acquisition system;
   processing a corresponding image in an image processing unit by using the acquired image data;
   detecting defects of the wafer surface generated on the corresponding image in a defect-detecting unit;
   computing a density of defects detected from the corresponding image in a density-counting unit;
   comparing a defect density of a previous image acquired in a defect detection performed before acquiring the corresponding image with a defect density of the corresponding image in a density comparison unit; and
   varying a horizontal moving speed of the stage by a scanning speed decision unit for a subsequent defect detection on the basis of a difference between defect densities, so as to control a wafer scanning speed by a scanning speed decision unit, wherein when the defect density of the corresponding image is reduced as compared with the defect density of the previous image, increasing the scanning speed of the image acquisition system.

4. The method of claim 3, wherein the defect density of the corresponding image is stored in a database, and outputting a defect density of the previous image from the database to the density comparison unit.

5. The method of claim 3, wherein when the defect density of the corresponding image increases as compared with the defect density of the previous image, reducing the scanning speed of the image acquisition system.

6. The method of claim 3, wherein when the defect density of the corresponding image is the same as or similar to the defect density of the previous image, maintaining a horizontal movement of the stage at a same speed.

7. The method of claim 3, wherein the defect density is acquired by one of counting the number of defects generated within the corresponding image and computing an area rate of defect within the corresponding image.

8. A surface inspection method comprising:
   loading a wafer on a predetermined position of a horizontally movable stage;
   determining a scanning section for an inspection area corresponding to a patterning area of the wafer;
   projecting and enlarging light reflected from a surface of the wafer within the scanning section, and acquiring an image corresponding to a surface of the wafer by an image acquisition system;
   detecting a defect of the image in a defect-detecting unit;
   computing a density of defects in a density-counting unit;
   comparing an increase/decrease of defect density in a density comparison unit; and
   varying a scanning speed according to an increase/decrease result of the defect density by a scanning speed decision unit.

9. The method of claim 8, wherein the scanning speed is a horizontal moving speed of the stage supporting the wafer.

10. The method of claim 8, wherein the increase/decrease comparison of the defect density is performed by comparing respective defect densities represented on a plurality of images continuously obtained from the image acquisition system.

11. The method of claim 10, wherein the plurality of images is divided into a plurality of segments, and comparing defect densities within the plurality of segments with one another.

12. The method of claim 8, wherein information corresponding to the defect density counted in the density-counting unit is stored in a database.

13. The method of claim 12, wherein the density comparison unit receives the density of defects and a previous defect density acquired in a previous defect detection from the density counting unit and the database, respectively, and compares them.

14. The method of claim 13, wherein when the corresponding defect density is reduced as compared with the previous defect density, increasing a scanning speed of the image acquisition system.

15. The method of claim 13, wherein when the corresponding defect density increases as compared with the previous defect density, reducing the scanning speed of the image acquisition system.

16. The method of claim 13, wherein when the corresponding defect density is the same as or similar to the previous defect density, maintaining a horizontal movement of the stage at a same speed.

17. The method of claim 8, wherein the defect density is acquired by one of counting the number of defects generated within the image and computing an area rate of defect within the image.

* * * * *